(12) United States Patent
Ying et al.

(10) Patent No.: US 10,080,737 B2
(45) Date of Patent: Sep. 25, 2018

(54) POLYMER-BASED HYDROTROPES FOR HYDROPHOBIC DRUG DELIVERY

(71) Applicant: Nitto Denko Corporation, Osaka (JP)

(72) Inventors: Wenbin Ying, San Diego, CA (US); Kwok Yin Tsang, Irvine, CA (US); Hao Bai, San Diego, CA (US); Haiqing Yin, San Marcos, CA (US); Jihua Liu, San Marcos, CA (US); Li Wang, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/679,404

(22) Filed: Apr. 6, 2015

(65) Prior Publication Data

US 2015/0283253 A1    Oct. 8, 2015

Related U.S. Application Data

(60) Provisional application No. 61/976,354, filed on Apr. 7, 2014.

(51) Int. Cl.
| | | |
|---|---|---|
| *A61K 47/48* | (2006.01) | |
| *A61K 31/337* | (2006.01) | |
| *A61K 31/395* | (2006.01) | |
| *C08G 69/48* | (2006.01) | |
| *C08G 69/10* | (2006.01) | |
| *A61K 47/64* | (2017.01) | |

(52) U.S. Cl.
CPC .......... *A61K 31/395* (2013.01); *A61K 31/337* (2013.01); *A61K 47/645* (2017.08); *C08G 69/10* (2013.01); *C08G 69/48* (2013.01)

(58) Field of Classification Search
CPC ............ A61K 47/488; A61K 47/48207; A61K 31/337; A61K 31/395; C08G 69/48
See application file for complete search history.

(56) References Cited

U.S. PATENT DOCUMENTS

| | | | |
|---|---|---|---|
| 4,966,773 A | 10/1990 | Gressel et al. | |
| 5,234,604 A | 8/1993 | Liao et al. | |
| 5,643,584 A | 7/1997 | Farng et al. | |
| 5,811,119 A | 9/1998 | Mehta et al. | |
| 5,851,538 A | 12/1998 | Froix et al. | |
| 6,183,774 B1 | 2/2001 | Aust et al. | |
| 8,178,124 B2 | 3/2012 | Niitsu et al. | |
| 8,173,170 B2 | 5/2012 | Niitsu et al. | |
| 8,574,623 B2 | 1/2013 | Niitsu et al. | |
| 8,652,526 B2 | 2/2014 | Niitsu et al. | |
| 8,686,052 B2 | 4/2014 | Niitsu et al. | |
| 2002/0012998 A1 | 1/2002 | Gonda et al. | |
| 2003/0096739 A1 | 5/2003 | Morris | |
| 2003/0161791 A1 | 8/2003 | Bentley et al. | |
| 2003/0211143 A1 | 11/2003 | Liu et al. | |
| 2004/0028682 A1 | 2/2004 | Border et al. | |
| 2005/0004064 A1 | 1/2005 | Tei et al. | |
| 2005/0165227 A1 | 7/2005 | Vlahov et al. | |
| 2006/0013775 A1 | 1/2006 | Gristwood et al. | |
| 2006/0074041 A1 | 4/2006 | Johnston et al. | |
| 2007/0010652 A1 | 1/2007 | Angot et al. | |
| 2007/0160568 A1 | 7/2007 | Angot et al. | |
| 2008/0057030 A1 | 3/2008 | Crager | |
| 2008/0279765 A1 | 11/2008 | Chettibi et al. | |
| 2009/0105179 A1 | 4/2009 | Yu et al. | |
| 2010/0028416 A1 | 2/2010 | Yu et al. | |
| 2011/0104255 A1 | 5/2011 | Niitsu et al. | |
| 2011/0178157 A1 | 7/2011 | Jin et al. | |
| 2011/0229558 A1 | 9/2011 | Niitsu et al. | |
| 2012/0269886 A1 | 10/2012 | Niitsu et al. | |
| 2012/0328694 A1 | 12/2012 | Niitsu et al. | |
| 2013/0011336 A1 | 1/2013 | Niitsu et al. | |
| 2013/0045272 A1 | 2/2013 | Niitsu et al. | |
| 2013/0136789 A1 | 5/2013 | Niitsu et al. | |
| 2013/0171127 A1 | 7/2013 | Niitsu et al. | |
| 2013/0171240 A1 | 7/2013 | Niitsu et al. | |
| 2013/0172401 A1 | 7/2013 | Niitsu et al. | |
| 2013/0210744 A1 | 8/2013 | Niitsu et al. | |
| 2013/0216611 A1 | 8/2013 | Niitsu et al. | |
| 2013/0267581 A1 | 10/2013 | Niitsu et al. | |
| 2014/0127187 A1 | 5/2014 | Niitsu et al. | |
| 2014/0315975 A1 | 10/2014 | Niitsu et al. | |
| 2014/0323550 A1 | 10/2014 | Ayabe et al. | |

FOREIGN PATENT DOCUMENTS

| | | |
|---|---|---|
| CN | 101321806 A | 12/2008 |
| CN | 101678123 A | 3/2010 |
| CN | 102159247 A | 8/2011 |
| EP | 1842557 | 10/2007 |
| JP | 08-268906 | 10/1996 |
| JP | 11-269076 | 10/1999 |
| JP | 2002-047211 | 2/2002 |
| JP | 2002-363094 | 12/2002 |
| JP | 2002-371006 | 12/2002 |
| JP | 2003-119138 | 4/2003 |
| JP | 2003-219893 | 8/2003 |
| JP | 2006-503124 | 1/2006 |
| JP | 2007-501321 | 1/2007 |
| JP | 2009-518511 | 5/2009 |
| JP | 2011-529492 | 12/2011 |

(Continued)

OTHER PUBLICATIONS

Jones (European Journal of Pharmaceutics and Biopharmaceutics 48 (1999) 101-111).*

(Continued)

*Primary Examiner* — Matthew P Coughlin
*Assistant Examiner* — Thurman M Wheeler
(74) *Attorney, Agent, or Firm* — Knobbe, Martens, Olson & Bear, LLP

(57) ABSTRACT

Polymer conjugates characterized in that the backbone of the polymer is an anionic polymer and hydrophobic moieties are covalently attached to the polymer backbone are useful for preparing drug encapsulated polymer hydrotropes and compositions. Such materials are useful in methods for delivering the drug into cells, and for the treatment and alleviation of diseases and disorders such as cancer.

15 Claims, 8 Drawing Sheets

(56) References Cited

FOREIGN PATENT DOCUMENTS

| WO | WO 1991/004748 | 4/1991 |
|---|---|---|
| WO | WO 2000/064478 | 11/2000 |
| WO | WO 2003/009881 | 2/2003 |
| WO | WO 2003/045383 | 6/2003 |
| WO | WO 2004/001381 | 12/2003 |
| WO | WO 2004/019921 | 3/2004 |
| WO | WO 2004/069159 | 8/2004 |
| WO | WO 2004/090108 | 10/2004 |
| WO | WO 2005/082402 | 9/2005 |
| WO | WO 2006/068232 | 6/2006 |
| WO | WO 2007/067417 | 6/2007 |
| WO | WO 2008/141107 | 11/2008 |
| WO | WO 2010/014117 | 2/2010 |
| WO | WO 2013/154707 | 10/2013 |

OTHER PUBLICATIONS

Kim2 (Journal of Pharmaceutical Sciences, vol. 99, No. 9, Sep. 2010).*
Lee et al., Pharmaceutical Research, vol. 20, 2003, 1022-1030.
Kim et al., "Hydrotropic polymer micelles as versatile vehicles for delivery of poorly water-soluble drugs" Journal of Controlled Release, vol. 152, 2011, 13-20.
Baek et al., "Aqueous N,N-diethylnicotinamide (DENA) solution as a medium for accelerated release study of paclitaxel" J. Biomater. Sci. Polymer Edn, vol. 15, No. 4, pp. 527-542 (2004).
Van et al., "Synthesis, characterization, and biological evaluation of poly(L-γ-glutamyl-glutamine)-paclitaxel nanoconjugate" Int J Nanomedicine. 2010; 5: 825-837.
Xu et al., "Targeting receptor-mediated endocytotic pathways with nanoparticles: rationale and advances" Adv Drug Deliv Rev. 2013; 65(1):121-38.
Yu et al., "Receptor-targeted nanocarriers for therapeutic delivery to cancer" Mol Membr Biol. 2010; 27(7):286-98.
Kamaly et al., "Targeted polymeric therapeutic nanoparticles: design, development and clinical translation" ChemSoc Rev. 2012;41(7):2971-3010.
Remington's Pharmaceutical Sciences, Mack Publishing Co., Easton, PA, 18th edition, 1990.
Fingl et al. 1975, in "The Pharmacological Basis of Therapeutics".
Ying et al., "A novel polymer-anticancer drug micelle formulation showing enhanced efficacy over Abraxane" American Association for Cancer Research Annual Meeting 2014 Presentation Abstract No. 4578.
Presentation Poster for AACR Annual Meeting 2014, No. 4578.
Andrew, E.R., et al., "Molecular motion in solid all-trans retinoic acid (vitamin A acid) by proton NMR." Solid State Nuclear Magnetic Resonance 13, pp. 39-43, 1998.
Beljaars, L., et al. "Albumin Modified With Mannosa 6-Phosphate: A Potential Carrier for Selective Delivery of Antifibrotic Drugs to Rat and Human Hepatic Stellate Cells." Hepatology vol. 29, No. 5, pp. 1486-1493, 1999.
Blomhoff et al., "Hepatic Uptake of [H] Retinol Bound to the Serum Retinol Binding Protein Involves Both Parenchymal and Perisinusoidal Stellate Cells," The Journal of Biological Chemistry 1985; 260(25): 13571-13575.
Blomhoff, Rune, et al., Newly Administered [³H] Retinol is Transferred from Hepatocytes to Stellate Cells in Liver for Storage. Experimental Cell Research, vol. 150, pp. 186-193, 1984.
Devi, GR. "siRNA-based Approaches in Cancer Therapy", Cancer Gene Therapy (2006) 13, 819-29.
Dixon et al., "Nomenclature of Retinoids." Pure & Appl. Chem., vol. 55, No. 4, pp. 721-726 (1983).
Dunham et al., Membrane fusion: Studies with a calcium-sensitive dye, arsenazo III, in liposomes. Proceedings of the National Academy of Science, USA, vol. 74, No. 4, pp. 1580-1584, 1997.
Fortuna V.A. et al., "Hepatic Stellate Cells Uptake of Retinol Associated With Retinol-Binding Protein or With Bovine Serum Albumin," Journal of Cellular Biochemistry 2003; 90(4):792-805.

Friedman, S. L., "Targeting siRNA to arrest fibrosis," Nature Biotechnology (Apr. 2008) 26(4): 399-400.
Goodman et al., "Extraction and Recombination Studies of the Interaction of Retinol with Human Plasma Retinol-Binding Protein." Journal of Lipid Research, vol. 13, 1972, pp. 338-347.
Kamps, J.Aam. et al., "Massive targeting of liposomes, surface-modified with anionized albumins, to hepatic endothelial cells," Proceedings of the National Academy of Sciences USA 1997; 94(21):11681-11685.
Kang et al., "Mannose-6-phosphateyinsulin-like growth factor-II receptor is a retinoic acid." Proc. Natl. Acad. Sci., vol. 95, pp. 13671-13676, Dec. 1998.
Kikuchi, H., Liposomes based on nanotechnology. Past, present and future. Part II, Pharm Tech Japan 2003; 19(3):419-433.
Kim et al., "Folate-tethered emulsion for the target delivery of retinoids to cancer cells." European Journal of Pharmaceutics and Biopharmaceutics. 68:618-625. (2008).
Li, D. et al., "Liver fibrogenesis and the role of hepatic stellate cells: New insights and prospects for therapy," Journal of Gastroenterology and Hepatology 1999; 14(7):618-633.
Lim et al., "Formulation parameters determining the physicochemical characteristics of solid lipid nanoparticles loaded with all-trans retinoic acid." International Journal of Pharmaceutics. 243:135-146. (2002).
Ma et al., "Comparison of Stability for All-trans Retinoic Acid Nanosuspensions and Lipid Nanoparticle Formulations." International Conference on Complex Medical Engineering. 197-202. (2007).
Marcucci et al., "Active targeting with particulate drug carriers in tumor therapy: fundamentals and recent progress." Drug Discovery Today. 9(5):219-228. (2004).
Nastruzzi et al., "Liposome-associated retinoic acid increased in vitro antiproliferative effects on neoplastic cells" FEBS Letters (1990) 259(2):293-296.
Sato et al., "Resolution of liver cirrhosis using vitamin A-coupled liposomes to deliver siRNA against a collagen-specific chaperone", Nature Biotechnology (2008) 26(4):431-442.
Singh, et al. "Liposome encapsulated vitamin A compounds exhibit greater stability and diminished toxicity." Biophysical Chemistry, vol. 73, pp. 155-162, 1998.
Socaciu, et al., Different Ways to Insert Carotenoids into Liposomes Affect Structure and Dynamics of the Bilayer Differently. Biophysical Chemistry, vol. 99, pp. 1-15, 2002.
Torchilin et al., "Immunomicelles: Targeted pharmaceutical carriers for poorly soluble drugs." PNAS. 100(10):6039-6044. (2003).
Torchilin, V. P. "Drug Targeting," European Journal of Pharmaceutical Sciences. (2000) 11(2):81-91.
Torchilin, VP., "Targeted pharmaceutical nanocarriers for cancer therapy and imaging" The AAPS Journal (2007) 9(2):E128-47.
Tsuji, H. et al., "Targeting of liposomes surface-modified with glycyrrhizin to the liver. I. Preparation and biological disposition," Chemical & Pharmaceutical Bulletin 1991; 39(4):1004-08.
Vogel et al., "An immortalized rat liver stellate cell line (HSC-TS): a new cell model for the study of retinoid metabolism in vitro." Journal of Lipid Research, vol. 41, 2000, pp. 882-893.
Wassall, S.R., et al. "Retinoid-Phospholipid Interactions as Studied by Magnetic Resonance" Bulletin of Magnetic Resonance, vol. 9 No. 3, pp. 85-89, 1987.
Watanabe, et al., Treatment of idiopathic myelofiosis employing siRNA for heat shock protein 7 (siRNA/HSP47) encapsulated in liposomes, Blood (2007) 110:235.
Whitmer et al., Membrane-membrane interactions associated with rapid transfer of liposomal bilirubin to microsomal UDP-glucuronyltransferase. Biochemical Journal, vol. 244, pp. 41-47, 1987.
Wu, J. et al., "Modification of liposomes for liver targeting," Journal of Hepatology (1996)24(6):757-763.
Zhang et al., "Cationic lipids and polymers mediated vectors for delivery of siRNA," J. Control Release (2007) 123: 1-10.
Zhao et al.; "Tumor-selective targeted delivery of genes and antisense oligodeoxyribonucleotides via the folate receptor," Advanced Drug Delivery Reviews (2004) 56: 1193-1204.

(56) References Cited

OTHER PUBLICATIONS

Office Action dated Apr. 23, 2018 for Chinese Application No. 201480077633.0.
Office Action dated Jun. 7, 2018 for Russian Application No. 2016143395/04.
Examination Report dated Mar. 6, 2018 for Australian Patent Application No. 2014390729.
Office Action dated Feb. 26, 2018 for Russian Patent Application No. 2016143395/04.
International Search Report and Written Opinion dated Dec. 19, 2014 for PCT Patent Application No. PCT/JP2014/004480.
International Preliminary Report on Patentability dated Oct. 12, 2016 for PCT Patent Application No. PCT/JP2014/004480.
Japanese Office Action dated Jun. 6, 2018 for Japanese Application No. 2016-561865.
Office Action dated Jun. 7, 2018 for Taiwanese Patent Application No. 103130601.

\* cited by examiner

POLYMER-BASED HYDROTROPES FOR HYDROPHOBIC DRUG DELIVERY

This application claims the benefit of U.S. Provisional Application No. 61/976,354, filed Apr. 7, 2014, the content of which is hereby incorporated by reference in its entirety.

FIELD

Disclosed herein are compositions and methods related to the fields of organic chemistry, pharmaceutical chemistry, biochemistry, molecular biology and medicine. In particular, embodiments disclosed herein relate to polymer conjugates for preparing drug encapsulated polymer hydrotropes, compositions and methods for delivering the drug into cells, and to the use of the compositions for the treatment and alleviation of diseases and disorders such as cancer.

BACKGROUND

Polymer micelles are one of widely used drug delivery systems (DDSs) for solubilizing various poorly soluble drugs such as a large portion of anticancer drugs, and also for delivery of the drug to the target site. Usually, block copolymers, composed of water-soluble polyethylene glycol (PEG) and water-insoluble polymer, are utilized to form polymer micelles, providing a hydrophilic outer shell and a hydrophobic inner core. The poorly soluble drugs are encapsulated in the latter via hydrophobic interaction with the hydrophobic portion of the copolymer and stay within the hydrophilic outer shell. As for PEG-based block copolymer micelles, poly(amino acid) complex of PEG-based copolymers such as PEG-block-poly(α,β-aspartic acid) and PEG-block-poly(L-lysine) are reported as remarkable functional materials for DDS.

Recently, hydrotropic compounds are drawing attention as useful compounds for improving solubility of the hydrophobic drugs. It was previously reported that diethylnicotinamide was identified to improve the solubility of paclitaxel in a dose depending manner from a screening for over 60 commercially available hydrotropes (Kinam et al., *Pharmaceutical Research*, Vol. 20, 2003, 1022-1030). After this report, the same author further reported that PEG-based block copolymers bearing diethylnicotinamide (DENA) and dimethylbenzamide (DMBA) moiety were able to encapsulate paclitaxel (Kinam etal., *Journal of Controlled Release*, Vol. 152, 2011, 13-20). Further, it has been reported that DENA was a hydrotropic agent for paclitaxel and improved a release profile of paclitaxel in poly(lactic-co-glycolic acid) (PLGA) matrices (Baek et al., *J. Biomater. Sci. Polymer Edn*, Vol. 15, No. 4, pp. 527-542 (2004)).

SUMMARY

One aspect of the invention described herein is directed to a polymer conjugate characterized in that the backbone of the polymer is an anionic polymer and hydrophobic moieties are covalently attached to the backbone of the polymer.

Some embodiments are related to a polymer conjugate described herein, which is composed of monomer units represented by the formula (I) and optionally the formula (II):

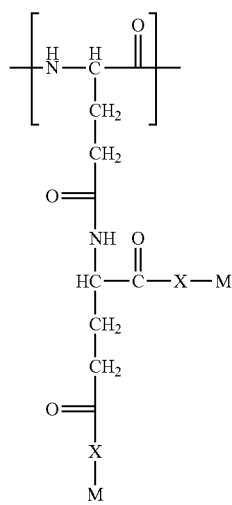

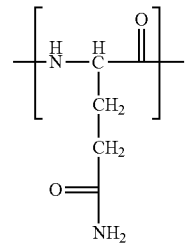

wherein, M is independently selected from the group consisting of hydrophobic moiety or cation; in which the hydrophobic moiety occupies 20-50 mol % of total M amount in the polymer, and the cation is independently selected from hydrogen, ammonium, or alkali metal; X is independently selected from the group consisting of O, S and NR; and R is selected from the group consisting of H, $C_{1-4}$ alkyl, $C_{2-4}$ alkenyl, $C_{2-4}$ alkynyl, aryl, and heteroaryl.

Some embodiments are related to a polymer conjugate described herein, which is represented by the formula (III)

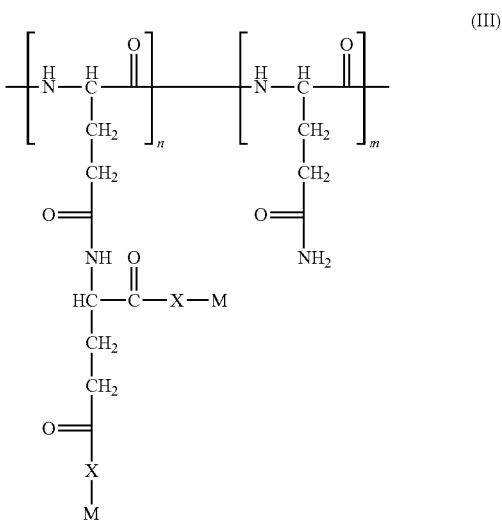

wherein, m and n are both an integer, where m is 0 or defined such that the ratio of m:n is from 1:9 to 5:5, and M and X are as defined above.

Some embodiments are related to a polymer conjugate described herein, wherein hydrophobic moiety is represented by the formula (IV);

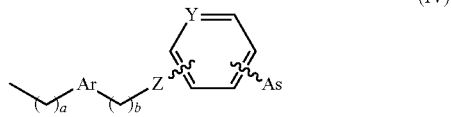

(IV)

wherein, a and b are independently an integer of 0 to 4; Ar is independently an aryl or heteroaryl; Z is independently selected from the group consisting of O, S, SO, $SO_2$, NR, and $CR_2$; Y is CH or N; As is one to three substituents independently selected from the group consisting of halides, OR, $NR_2$, COOR, $CONR_2$, and CN; and R is independently selected from the group as described herein.

Some embodiments are related to a polymer conjugate described herein, wherein As is one $CONR_2$ substituent.

Some embodiments are related to a polymer conjugate described herein, wherein R is selected from ethyl or methyl.

Some embodiments are related to a polymer conjugate described herein, wherein a and b are both 1.

Some embodiments are related to a polymer conjugate described herein, wherein Ar is aryl.

Some embodiments are related to a polymer conjugate described herein, wherein Z is O.

Some embodiments are related to a polymer conjugate described herein, wherein the hydrophobic moiety is independently selected from

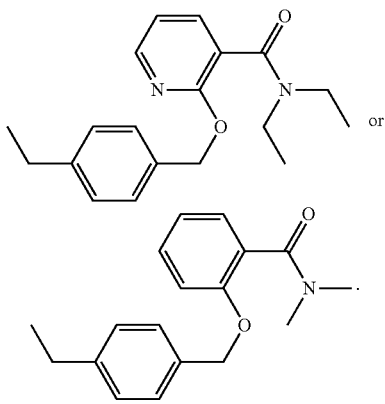

Another aspect of the invention is directed to a polymer micelle derived from the polymer conjugate described herein.

Another aspect of the invention is directed to a composition comprising the polymer conjugate carrier described herein and a hydrophobic compound operatively associated with the carrier.

Another aspect of the invention is directed to a therapeutic composition comprising the polymer conjugate carrier described herein and a hydrophobic drug operatively associated with the carrier.

Some embodiments are related to a therapeutic composition described herein, wherein the hydrophobic drug is an anticancer drug.

Some embodiments are related to a therapeutic composition described herein, wherein the drug is selected from the group consisted of paclitaxel, docetaxel, tanespimycin, griseofulvin, nifedipine, progesterone and probucol.

Some embodiments are related to a therapeutic composition described herein, wherein the drug is selected from the group consisted of paclitaxel, docetaxel, and tanespimycin.

Some embodiments are related to a therapeutic composition described herein, wherein the polymer conjugate forms a polymer micelle and the hydrophobic therapeutic agent is encapsulated in the polymer micelle.

Another aspect of the invention is directed to a method for treating a disease or condition by administering to a subject in need thereof an effective amount of the therapeutic composition described herein for the treatment of the disease or condition.

Some embodiments are related to a method described herein, wherein the disease or condition is selected from the group consisting of cancer, infectious diseases, hypertension, angina, gynecological diseases, and hyperlipidemia.

Some embodiments are related to a method described herein, wherein the disease or condition is cancer.

These and other embodiments are described in greater detail below.

DETAILED DESCRIPTION

Figure 1:
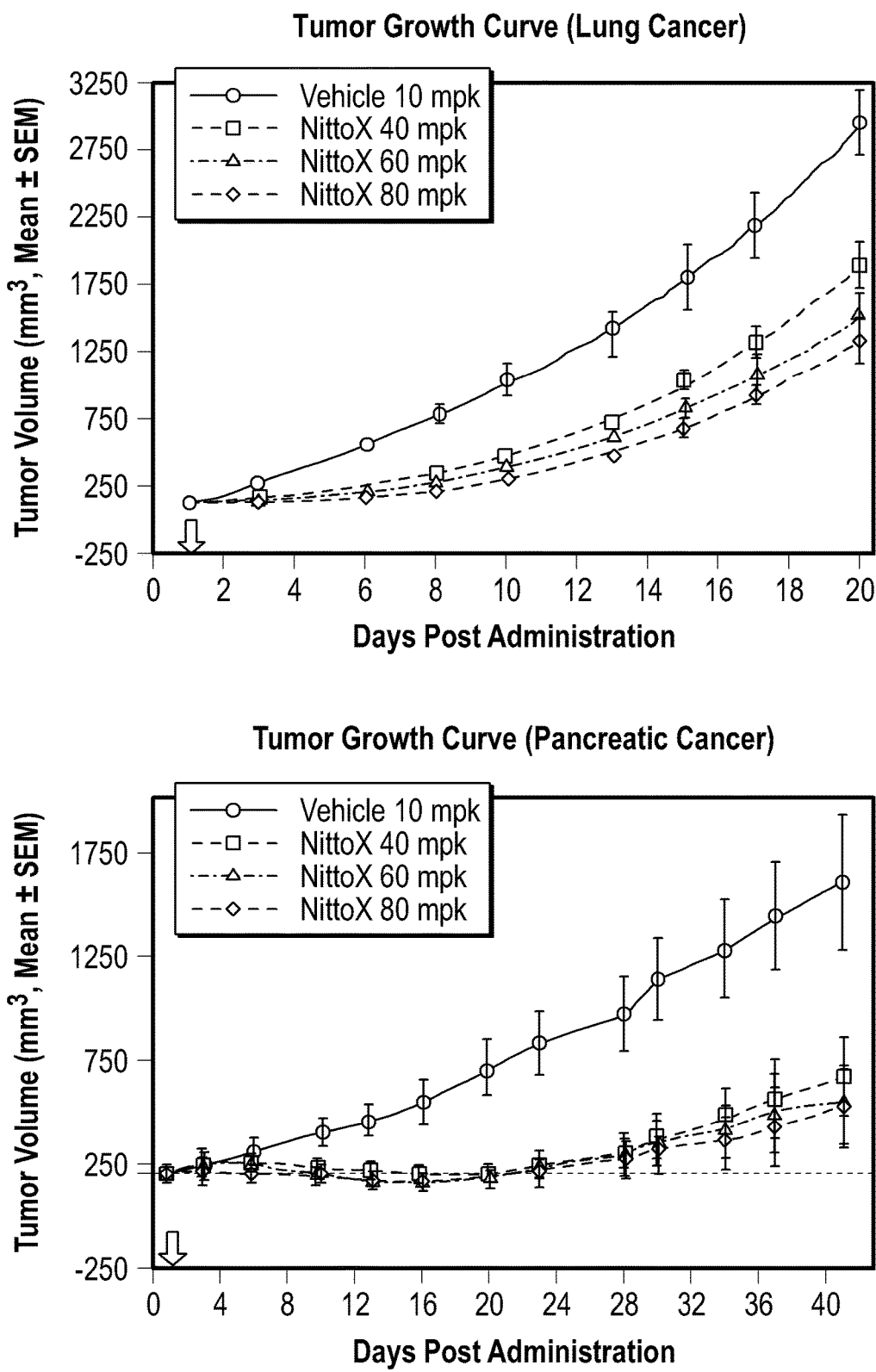
FIG. 1 illustrates tumor growth curves for lung cancer (upper) and pancreatic cancer (lower), respectively. PTX-PGGA-Hydrotrope III (Nitto X) was demonstrated to be able to suppress the tumor growth in a dose dependent manner.

Unless defined otherwise, all technical and scientific terms used herein have the same meaning as is commonly understood by one of ordinary skill in the art. All patents, applications, published applications and other publications referenced herein are incorporated by reference in their entirety. In the event that there is a plurality of definitions for a term, those in this section prevail unless stated otherwise.

Polymer Conjugate

One aspect of the invention provides a polymer conjugate in that the backbone is an anionic polymer and hydrophobic moieties are covalently attached to the polymer backbone. The polymer conjugate of the invention may comprise a polymer backbone equipped with anionic, hydrophilic side chain, e.g., poly-(L-γ-glutamylglutamine) (PGGA, see e.g., WO 2007/067417, WO2010/014117 and Sang Van et al., Int J Nanomedicine. 2010; 5: 825-837, which is incorporated herein its entirety by reference), as well as hydrophobic moieties, e.g., diethylnicotinamide (DENA) and dimethylbenzamide (DMBA). The latter is covalently attached to the backbone as part of side chains. Based on the strong interaction between the hydrophobic compounds and the hydrophobic moiety attached to the backbone in aqueous medium, the former could be easily encapsulated by the polymer conjugate producing water soluble polymer micelles using common quick mixing methods. Since the backbone of the polymer conjugate is anionic, i.e., negatively charged, the polymer micelles prepared from the polymer conjugate of the invention should not associate with plasma proteins or cell membranes, which are also mainly negatively charged too. This not only enhances their mobility, but also prolongs the plasma circulation time for delivery to the tumor sites. Besides, the interaction between the hydrophobic drug and the polymer micelles described herein are less than those in the traditional PEG-copolymer based polymer micelles, as reflected by the former having a lower critical micelle concentration (CMC). This implies that drug encapsulated polymer micelles of the invention described herein are relatively easier to release their drug load and enhance the therapeutic efficacy at the tumor sites.

As mentioned above, PEG-based copolymers are conventionally used for the polymer micelle conjugates so far. One problem of PEG-based copolymers is the non-biodegradable nature of PEG. Therefore, in some preferred embodiments of the invention described herein, the polymer conjugate is biodegradable. The biodegradable polymers used for making the polymer conjugates of the invention described herein are not limited as far as it does not adversely affect the interaction between the hydrophobic compound and the polymer conjugate. Examples of the biodegradable polymers include, but are not limited to, poly-(L-γ-glutamylglutamine) (PGGA), poly-L-glutamic acid (PGA), poly-(γ-L-aspartylglutamine) (PGAA), poly-(lactic acid-co-glycolic acid) (PLGA), and mixtures thereof.

Some embodiments of the invention described herein provide a polymer conjugate which is comprised of monomer units represented by the formula (I) and optionally formula (II) below:

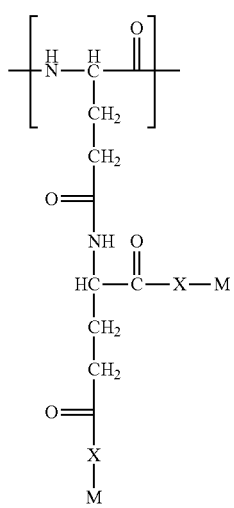

(I)

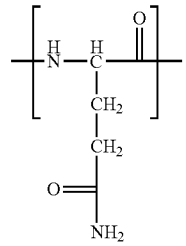

(II)

wherein,
M is independently selected from the group consisting of hydrophobic moiety or cation; in which the hydrophobic moiety occupies 20-50 mol % of total M amount; and the cation is independently selected from hydrogen, ammonium, or alkali metal;
X is selected from the group consisting of O, S and NR; and
R is selected from the group consisting of H, $C_{1-4}$ alkyl, $C_{2-4}$alkenyl, $C_{2-4}$alkynyl, aryl, and heteroaryl.

As used herein, "aryl" refers to a carbocyclic (all carbon) monocyclic or multicyclic aromatic ring system that has a fully delocalized pi-electron system. Examples of aryl groups include, but are not limited to, benzene, naphthalene and azulene. As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur.

As used herein, "alkyl" refers to a straight or branched hydrocarbon chain fully saturated (no double or triple bonds) hydrocarbon group. "$C_{1-4}$ alkyl" indicates that there are one to four carbon atoms in the alkyl chain, i.e., the alkyl chain is selected from the group consisting of methyl, ethyl, propyl, iso-propyl, butyl, iso-butyl, sec-butyl, and tert-butyl. Typical alkyl groups include, but are not limited to, methyl, ethyl, propyl, isopropyl, butyl, isobutyl, tertiary butyl, and the like. As used herein, "alkenyl" refers to an alkyl group that contains in the straight or branched hydrocarbon chain bearing one or more double bonds. As used herein, "alkynyl" refers to an alkyl group that contains in the straight or branched hydrocarbon chain with one or more triple bonds.

As used herein, "hydrophobic moiety" refers to a moiety which is attached to a polymer side chain and interacts with another hydrophobic moiety or hydrophobic drugs. Any hydrophobic moiety known in the art could be used for the invention as long as it does not adversely affect the properties of the polymer conjugate. In some embodiments, "hydrophobic moiety" may include, but not limited to, any water-insoluble monocyclic or multicyclic aromatic ring or carbocycle systems. In some embodiments, hydrophobic moiety may include DENA, DMBA, adamantine, phenyl, naphthalene, cholesterol, a water-insoluble derivative thereof, and the like. In preferred embodiments, hydrophobic moiety is selected from the group consisting of DENA and DMBA.

As used herein, "cation" refers to a counter ion of the anionic group, e.g., carboxyl group on the side chain of the polymer backbone. Examples of cation may include, but are not limited to, hydrogen, ammonium, alkali metal, and alkali earth metal. In one embodiment, cation is sodium.

The molecular weight of the polymer backbone may vary. In some embodiments, the molecular weight of the polymer backbone can be in the range of about 15 kDa to about 80 kDa.

In some embodiments of the invention described herein provide a polymer represented by the formula below:

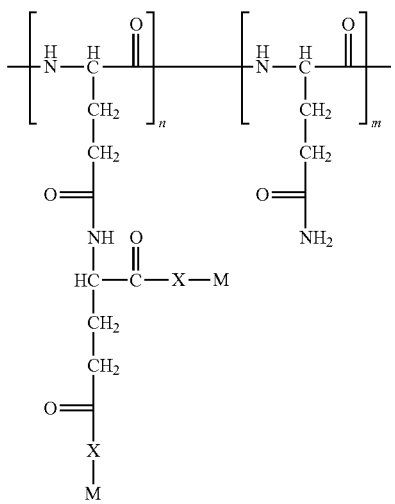

(III)

wherein, m and n are both an integer, where m is 0 or defined such that the ratio of m:n is from 1:9 to 5:5, and M and X are as defined above.

In some embodiments, the hydrophobic moiety is represented by the formula (IV);

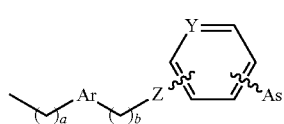

(IV)

wherein, a and b are independently an integer of 0 to 4, preferably both 1;

Ar is independently an aryl or heteroaryl, preferably aryl;

Z is independently selected from the group consisting of O, S, SO, SO$_2$, NR, CR$_2$, preferably O;

Y is CH or N;

As is one to three substituents independently selected from the group consisting of halides, OR, NR$_2$, COOR, CONR$_2$, and CN, preferably CONR$_2$; and R is independently selected from the group as defined above, preferably ethyl or methyl.

In some preferred embodiments, the hydrophobic moiety is independently selected from

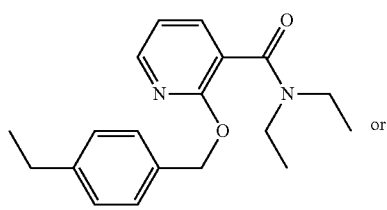

or

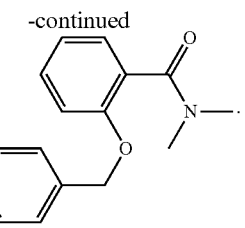

The polymer conjugate described above is able to aggregate and form a polymer micelle. Thus, one aspect of the present invention encompasses the polymer micelle which is formed by the polymer conjugate described herein.

The polymer conjugate described herein could be produced by the conventional procedure, such as dehydrated condensation of hydrophobic moiety with polymer backbone carboxylic residue. Non-limiting examples of the preparation of the polymer conjugates of the invention are described in below.

The polymer conjugate described herein may be used as a carrier for transporting a compound, in particular a hydrophobic compound (such as hydrophobic drug), in the body. The polymer conjugate described herein may be used to form a polymer micelle as a nanoparticulate carrier, which may be used for transporting the encapsulated compound to tumor site in the body.

Composition

Another aspect of the invention described herein provides a composition comprising a polymer conjugate carrier described above and a hydrophobic compound operatively associated with the hydrophobic moiety of the polymer conjugate to form a hydrophobic core. In some embodiments, the hydrophobic compound may be therapeutic drug, labeling compound, etc. In one embodiment, the composition is a therapeutic composition comprising of a polymer conjugate carrier described above and a hydrophobic drug operatively associated with the carrier.

As used herein, the term "carrier" may be used to refer to various types of substances, including a polymeric carrier or a micellar carrier. A carrier can be operatively associated with one or more compounds, e.g., a therapeutic drug and/or a targeting agent. In this context, "operatively associated" refers to an electronic interaction between the carrier and the agent(s). Such interaction may take the form of a chemical bond, including, but not limited to, a covalent bond, a polar covalent bond, an ionic bond, an electrostatic association, a coordinate covalent bond, an aromatic bond, a hydrogen bond, a dipole, or a van der Waals interaction. Those of ordinary skill in the art understand that the relative strengths of such interactions may vary widely.

The term "therapeutic" refers to the alleviation, prevention, or inhibition of any undesired signs or symptoms of a disease or condition to any extent. Such undesired signs may include those that worsen the subject's overall feeling of well-being or appearance. This term does not necessarily indicate total cure or abolition of the disease or condition. A "therapeutic drug" is a compound that, upon administration to a mammal in a therapeutically effective amount, provides a therapeutic benefit to the mammal. In some embodiment, a therapeutic agent may be hydrophobic drug. Those skilled in the art will appreciate that the term "therapeutic drug" is not limited to drugs that have received regulatory approval. A "therapeutic drug" can be operatively associated with at least one carrier and/or other agent.

In some preferred embodiments, polymer hydrotropes of the invention described herein contains modified PGGA-based polymer micelles. Since PGGA is proved to be highly water soluble, biocompatible, biodegradable, non-immunogenic, non-hemolytic, and versatile in making both polymer drug conjugates as well as polymeric micelle formulations, the PGGA-based polymer micelles would have the following advantageous points: i) high drug loading capacity; ii) elimination of the use of unnatural non-biodegradable PEG or other highly toxic solubilizing excipients; iii) enhanced tumor accumulation; iv) systemic toxicity reduction; and/or v) therapeutic efficacy enhancement.

A carrier may associate with some compounds other than the hydrophobic compound encapsulated in the polymer micelles. The examples of the compounds other than the hydrophobic compound encapsulated in the polymer micelles include, but are not limited to, label, targeting agents and additional therapeutic drugs. The additional therapeutic drugs may or may not be hydrophobic. Non-limiting examples of targeting agents, etc., may be found, e.g., in Xu et al., *Adv Drug Deliv Rev.* 2013; 65(1):121-38; Yu et al., *Mol Membr Biol.* 2010; 27(7):286-98 and Kamaly et al., *ChemSoc Rev.* 2012; 41(7):2971-3010.

In the embodiment of the aspect described herein, the therapeutic drug is not limited as far as it is hydrophobic. Examples of therapeutic drugs may include, but not limited to, families of taxanes, macrocyclicpolyketides, and resorcinylic isoxazole amides. In some embodiments, the therapeutic drugs may include, but are not limited to, paclitaxel, docetaxel, tanespimycin, griseofulvin, nifedipine, progesterone, probucol, clofibrate, coenzyme Q10, glibenclamide, felodipine, fenofibrate, itraconazole, anthracene and dihydroanthracene. In some embodiments, the therapeutic drug may be anticancer drug. The examples of the anticancer drug may include, but are not limited to, paclicaxel, docetaxel and tanespimycin. In another embodiment, the therapeutic drug may be antibiotics, hormones, and the like.

In some embodiments, the composition of the invention is the composition for use in treating diseases or in other words, pharmaceutical compositions, wherein the composition comprises the polymer conjugate described herein and the hydrophobic drug described herein. In some preferred embodiments, the diseases include, but are not limited to cancer, infectious diseases, hypertension, angina, gynecological diseases, endocrine diseases, and hyperlipidemia.

The pharmaceutical compositions described herein can be administered to a human patient per se, or in pharmaceutical compositions where they are mixed with other active ingredients, as in combination therapy, or suitable pharmaceutical carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compositions can also be administered in sustained or controlled release dosage forms, including depot injections, osmotic pumps, pills, transdermal (including electrotransport) patches, and the like, for prolonged and/or timed, pulsed administration at a predetermined rate.

Pharmaceutical compositions may be formulated in any conventional manner using one or more physiologically acceptable pharmaceutical carriers comprising excipients and auxiliaries, which facilitate processing of the active compounds into pharmaceutical preparations. Proper formulation is dependent upon the route of administration chosen. Any of the well-known techniques, pharmaceutical carriers, and excipients may be used as suitable and as understood in the art; e.g., in Remington's Pharmaceutical Sciences, above.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate, or ameliorate either symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the dosages will be about the same, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of each active ingredient, preferably about 1 mg to about 500 mg, e.g. 5 to 200 mg. In other embodiments, an intravenous, subcutaneous, or intramuscular dose of each active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free base. In some embodiments, the composition is administered 1 to 4 times per day. Alternatively the compositions may be administered by continuous intravenous infusion, preferably at a dose of each active ingredient up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Method

The invention described herein encompasses a method for treating a disease or condition via administering the therapeutic composition of the present invention to a subject in need thereof in an effective amount to achieve the intended purpose. The disease which may be treated is not limited, provided that the therapeutic drug is hydrophobic and the drug may improve the condition of the disease. The examples of the disease may include, but are not limited to, cancer, infectious diseases, hypertension, angina, gynecological diseases, endocrine diseases, and hyperlipidemia. In one embodiment, the disease is cancer.

The aspect of the invention encompasses the embodiment of administering the therapeutic composition described above. Therefore, examples described in the embodiment of the therapeutic composition above such as the examples for administration route, dosage forms, amounts subjects and the like would also be applicable to the method for treating diseases described herein.

EXAMPLES

The following examples are provided for the purposes of further describing the embodiments described herein, and do not limit the scope of the invention.

Synthesis of Polymer Hydrotropes

Example 1 pGG-DENA Polymer Hydrotropes

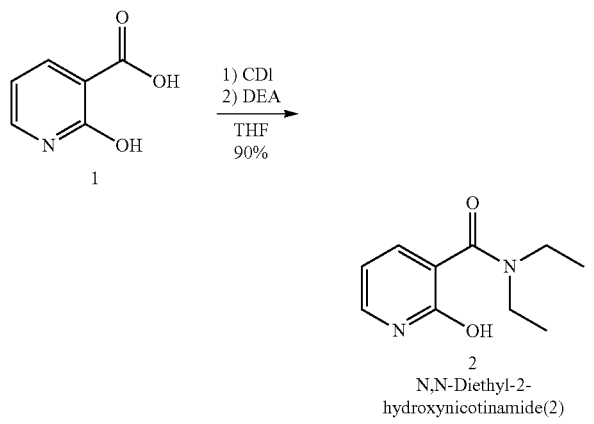

2-Hydroxynicotinic acid (1, 20 g, 143.8 mmol) was reacted with 1,1'-carbonyldiimidazole (CDI, 25.6 g, 158.2 mmol) in 900 mL of anhydrous THF at 70° C. After 24 hours, 400 mL of THF was added into the crude solution and 30 mL of diethylamine (DEA, 299.0 mmol) was then added dropwise. The reaction mixture was further heated at 70° C. for additional 18 hours. White crystal of N,N-diethyl-2-hydroxynicotinamide (2) was obtained by repeated recrystallization in 50 mL THF, (25.2 g, 90% yield).

LC-MS m/z=195.2[M+H]$^+$; $^1$HNMR (400 MHz, DMSO-$d_6$) δ 1.00 (t, 3H, J=6.96 Hz), 1.08 (t, 3H, J=6.96 Hz), 3.12 (q, 2H, J=6.96 Hz), 3.35 (q, 2H, J=6.96 Hz), 6.21 (t, 1H, J=6.60 Hz), 7.42 (m, 2H), 7.65 (s, 1H).

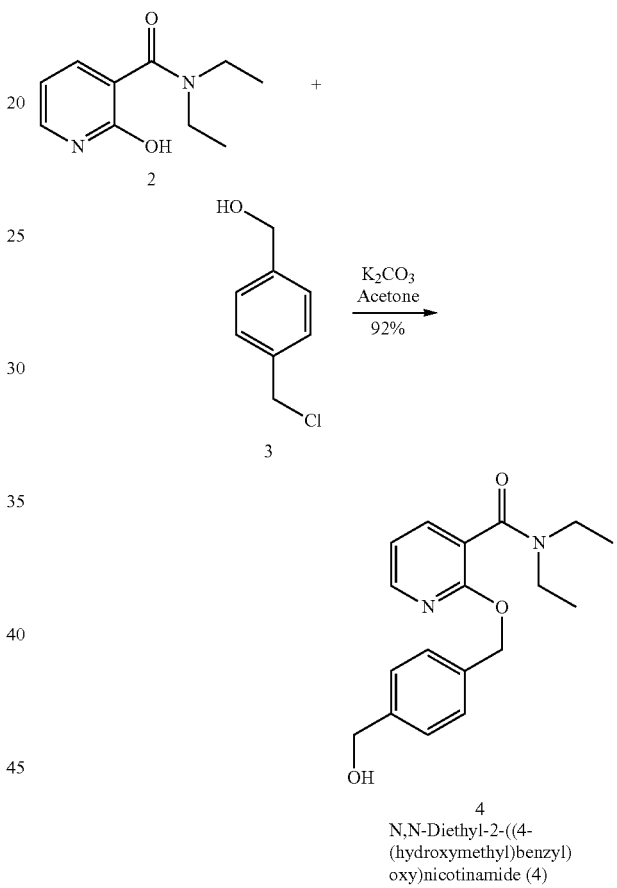

4
N,N-Diethyl-2-((4-(hydroxymethyl)benzyl)oxy)nicotinamide (4)

To a solution of N,N-diethyl-2-hydroxynicotinamide (2) (5 g, 25.7 mmol) in 150 mL of anhydrous acetone with $K_2CO_3$ (7.12 g, 51.5 mmol), (4-(chloromethyl)phenyl)methanol (3) was added dropwise at 60° C. and the reaction mixture was stirred under nitrogen for 20 hours. The crude reaction mixture was then filtered and the product was purified by flash column chromatography using 1:1/THF: Hex on silica gel. Further purification was performed by recrystallization from EtOAc/Hex to provide 7.31 g of N,N-diethyl-2-((4-(hydroxymethyl)benzyl)oxy)nicotinamide (4) as a crystalline white solid (90.3% yield).

LC-MS m/z=315.4 [M+H]$^+$, $^1$HNMR (400 Hz, CDCl$_3$) δ 1.09 (m, 3H), 1.21 (m, 3H), 2.29 (bs, 1H), 3.23 (m, 2H), 3.50 (m, 2H), 4.64 (d, 2H, J=5.48 Hz), 5.10 (bs, 2H), 6.17 (t, 1H, J=6.96 Hz), 7.28 (m, 6H).

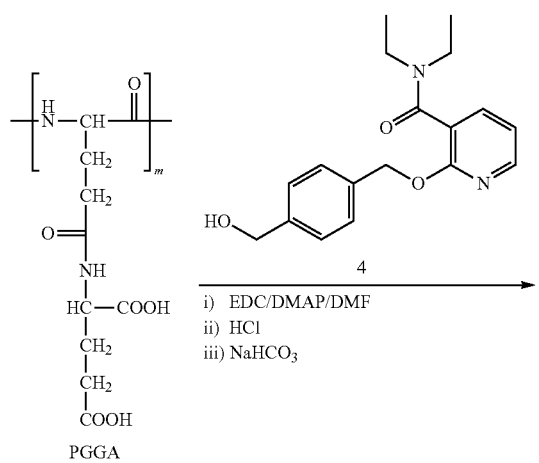

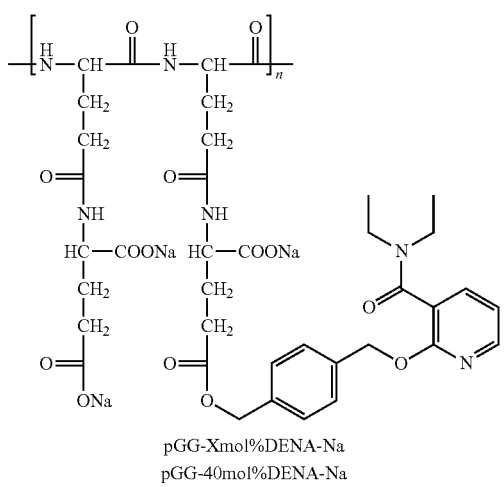

pGG-Xmol%DENA-Na
pGG-40mol%DENA-Na

To a solution of 100 mL of anhydrous DMF in a 250 mL of round bottom flask, 5.0 g of PGGA was added and the mixture was stirred at room temperature for 10 minutes until all solid material dissolved to give a clear solution. 5.57 g of 1-ethyl-3-(3-dimethylaminopropyl)carbodiimide (EDC) and 1.18 g of N,N-4-dimethylaminopyridine (DMAP) were then added sequentially. After stirred at room temperature for 15 minutes, 4.87 g of 4 was added in one potion and the resulting solution was stirred at ambient temperature for 28 hours. The reaction mixture was then poured slowly into 600 mL of 0.2 N HCl solutions stirred by a magnetic stir. After stirred for 10 minutes, the white crude product was isolated by centrifugation. The crude, after washed with 0.2 N HCl and MilliQ sequentially, was dissolved into 500 mL of 0.3N NaHCO$_3$ solution with stirring until a clear solution was obtained. The solution was first filtered and the filtrate was then purified by a TFF system (3 kDa, mPES column) until the permeate solution conductivity was less than 0.05 mS/cm. The retentate was finally lyophilized to provide 10.5 g of pGG-40 mol % DENA-Na conjugate (94% yield).

GPC-MALS: 83.2 kDa, PDI: 1.558, UV loading: 38%, $Z_{ave}$: 24 nm.

Other pGG-DENA-Na conjugates were also prepared using the same protocol with different quantities of 4.

Example 2 pGG-DMBA Polymer Hydrotropes

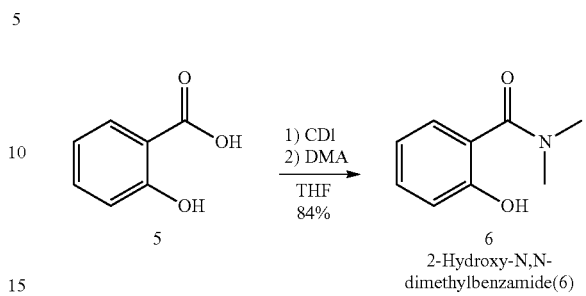

5

6
2-Hydroxy-N,N-dimethylbenzamide(6)

2-Hydroxybenzoic acid (7, 20 g, 144.8 mmol) was reacted with 1,1'-carbonyldiimidazole (CDI, 23 g, 159.3 mmol) in 900 mL of anhydrous THF at 70° C. After 20 hours, 145 mL of dimethylamine (DMA, 2.0M solution in THF, 290 mmol) was then added dropwise. The reaction mixture was further heated at 70° C. for additional 20 hours. After cooled to room temperature and removed the solvent at reduced pressure, the residue was diluted with EtOAc (1000 mL), and washed with 0.2 NHCl (2×800 mL) and brine (500 mL). The organic layer was finally dried over anhydrous Na$_2$SO$_4$, filtered, and concentrated to give a crude solid. The white crystal of 2-hydroxy-N,N-dimethylbenzamide (6) was obtained by recrystallization using EtOAc/Hexane (20 g, 84% yield).

LC-MS m/z=166.2[M+H]$^+$; $^1$HNMR (400 MHz, CDCl$_3$) δ 3.13 (s, 6H), 6.82 (t, 1H, J=5.56 Hz), 6.98 (d, 1H, J=5.56 Hz), 7.29 (m, 2H).

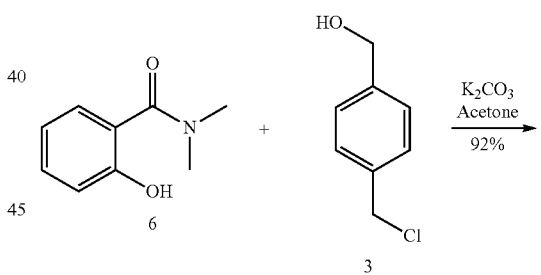

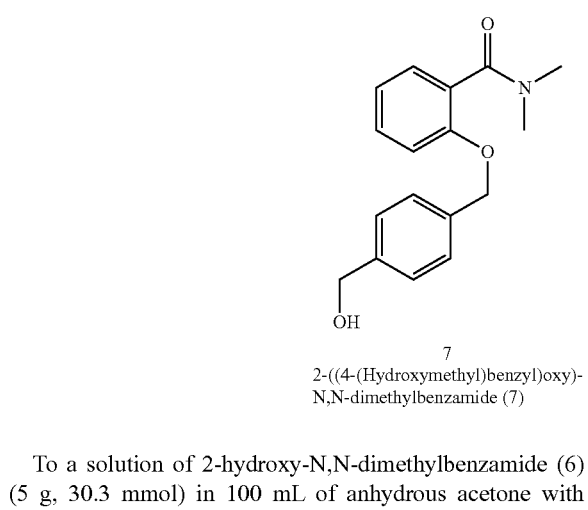

7
2-((4-(Hydroxymethyl)benzyl)oxy)-N,N-dimethylbenzamide (7)

To a solution of 2-hydroxy-N,N-dimethylbenzamide (6) (5 g, 30.3 mmol) in 100 mL of anhydrous acetone with K$_2$CO$_3$ (8.37 g, 60.5 mmol), (4-(chloromethyl)phenyl)methanol (1) (7.11 g, 45.4 mmol) was added dropwise at 60° C. and the reaction mixture was stirred at 65° C. under nitrogen for 20 hours. The crude reaction mixture was then filtered and the product was purified by flash column chromatography using 1:1/EtOAc:Hex on silica gel to provide 8.5 g of 2-((4-(hydroxymethyl)benzyl)oxy)-N,N-dimethylbenzamide (7) as crystalline white solid (92% yield).

LC-MS m/z=286.3 [M+H]$^+$, $^1$HNMR (400 Hz, CDCl$_3$) δ 2.37 (bs, 1H), 2.83 (s, 3H), 3.078 (s, 3H), 4.64 (s, 2H), 5.08 (s, 2H), 6.93 (m, 2H), 7.30 (m, 6H).

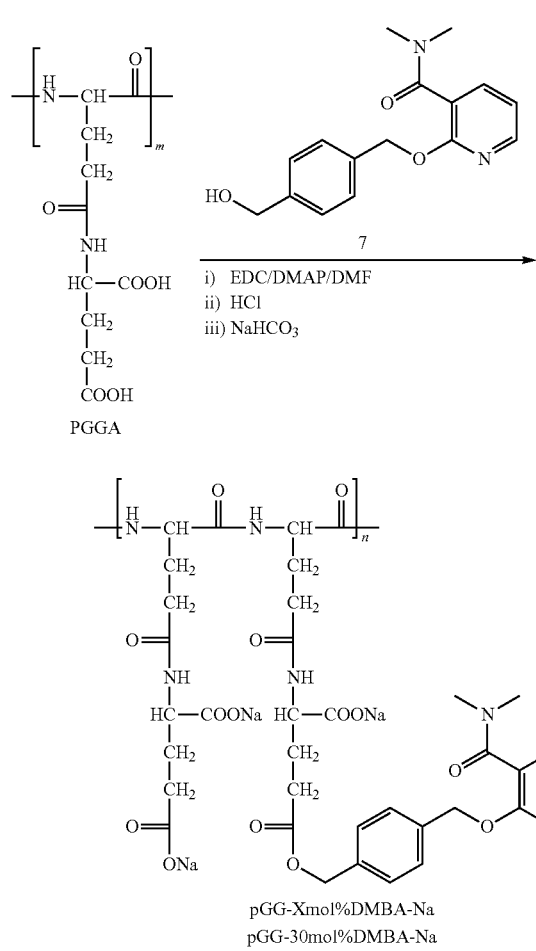

To a solution of 100 mL of anhydrous DMF in a 250 mL of round bottom flask, 5.0 g of PGGA was added and the mixture was stirred at room temperature for 10 minutes until all solid material dissolved to give a clear solution. 4.83 g of 1-ethyl-3-(3-dimethylaminopropyl)carbodiimide (EDC) and 0.71 g of N,N-4-dimethylaminopyridine (DMAP) were then added sequentially. After stirred at room temperature for 15 minutes, 3.32 g of 7 was added in one potion and the resulting solution was stirred at ambient temperature for 28 hours. The reaction mixture was then poured slowly into 600 mL of 0.2 N HCl solutions stirred by a magnetic stir. After stirred for 10 minutes, the white crude product was isolated by centrifugation. The crude, after washed with 0.2 N HCl and MilliQ sequentially, was dissolved into 500 mL of 0.3N NaHCO$_3$ solution with stirring until a clear solution was obtained. The solution was first filtered and the filtrate was purified by a TFF system (3 kDa, mPES column) until the permeate solution conductivity was less than 0.05 mS/cm. The retentate was finally lyophilized to provide 9.1 g of the title compound (97% yield).

GPC-MALS: 69.7 kDa, PDI: 1.417, UV loading: 29%, $Z_{ave}$: 20 nm.

Other pGG-DMBA-Na conjugates were also prepared using the same protocol with different quantities of 7.

Fabrication of Drug-encapsulated pGG-hydrotrope PMs

Example 3

Preparation of Drug-encapsulated pGG-hydrotrope Polymer Micelles

All drug-encapsulated pGG-hydrotrope PMs were prepared following the industrial standard quick mixing method. Briefly, an ethanol solution of drug and a solution of pGG-hydrotrope in PBS buffer in a given mass ratio are mixed rapidly at a T-joint by one peristaltic pump and the mixture is then quickly diluted with a buffer derived by another pump. A diafiltration system is then employed to remove the ethanol as well as concentrate the crude formulations. The final Ready-To-Use (RTU) dosage form will be available after filtration via a 0.2 μm membrane filtering medium. Examples of hydrophobic drugs that could be encapsulated by pGG-hydrotropes include paclitaxel, docetaxel, and tanespinmycin.

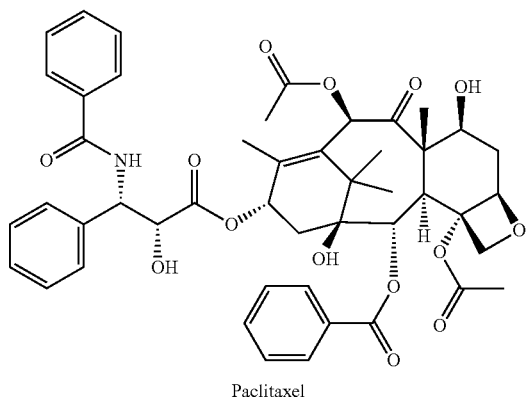
Paclitaxel

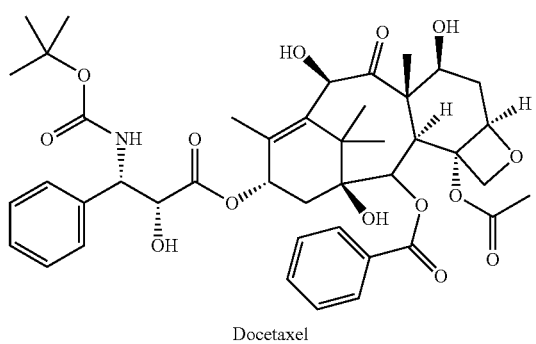
Docetaxel

-continued

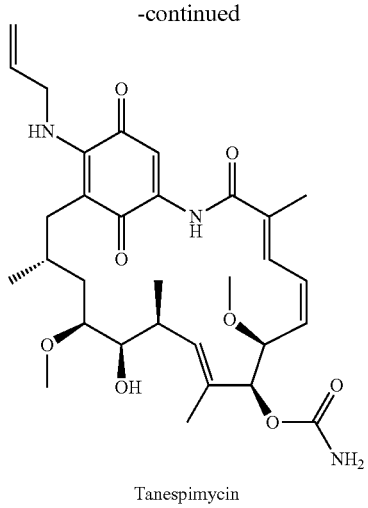

Tanespimycin

TABLE 1

Properties Of The Polymer Hydrotropes

| PGGA-Hydrotrope | Drug | Encapsulation Content (wt %) | Size (nm) | PDI |
|---|---|---|---|---|
| III | Paclitaxel | 31 wt % | 137 | 0.05 |
| IV | Paclitaxel | 30 wt % | 114 | 0.05 |
| I | Paclitaxel | 28 wt % | 14 | 0.12 |
| II | Paclitaxel | 27 wt % | 13 | 0.16 |
| I | Docetaxel | 7 wt % | 13 | 0.34 |
| II | Docetaxel | 21 wt % | 11 | 0.18 |
| II | Tanespimycin | 11.0 wt % | 138 | 0.08 |

Key: I = pGG-30 mol % DMBA; II = pGG-40 mol % DMBA; III = pGG-30 mol % DENA; IV = pGG-40mol % DENA.

The polymerhydrotropes of the invention described above have been demonstrated being capable of interacting with the hydrophobic drugs and form stable polymer micelles. From these polymer hydrotropes, paclitaxel encapsulated in pGG-30 mol % DENA polymer micelles (PTX-PGGA-Hydrotrope III, also referred to asNitto X) were used for the subsequent studies. The physical properties of PTX-PGGA-Hydrotrope III are shown in below table.

TABLE 2

Properties Of NittoX

| Size | Site distribution | pH | Surface charge |
|---|---|---|---|
| $Z_{ave}$ < 140 nm | 0.05 | 7.4 ± 0.5 | −40 mV |

In Vivo Efficacy Assay

Example 4

Establishment of Mia-Paca-2 Pancreatic Cancer Xenograft Model Tumor Xenograft

Mia-Paca-2 cell line was purchased from ATCC and maintained in RPMI-1640 supplemented with 10% Fetal Bovine Serum, 100 U/ml penicillin and 100 μg/ml streptomycin. Cells were harvested in the log phase of growth from the tissue culture after lightly trypsinized with trypsin-EDTA. The number of viable cells were counted and determined in a hemocytometer in the presence of trypan blue (only viable cells were counted). Each mouse was inoculated subcutaneously in the right flank with 0.1 mL of an inoculum of $2\times10^6$ of Mia-Paca-2 cells using a 25 G needle and syringe. (one inoculum per mouse). Tumor volume was monitored twice a week. Bodyweight measurements were also taken. Tumor volume was calculated using the formula: Tumor volume=(length×(width)$^2$)/2.

Example 5

Dose Response Effect

Once the tumors established in Example 4 reached approximately 200-220 mm$^3$ (average tumor volume at 209 mm$^3$), the mice were assigned into the vehicle control and various treatment groups, such that the mean tumor volumes in the treated groups were within 10% of the mean tumor volume in the vehicle control group, and the CV % of tumor volume was less than 25%. On the same day, freshly prepared test articles (e.g. PTX-encapsulated PGGA-hydrotrope III PMs, NittoX) and the vehicle control group was injected through a tail vein at dosages of 40, 60, and 80 mg (PTX equiv.)/kg at dosing volume of 10 mL/kg. Tumor volume was monitored twice a week. Bodyweight measurements were also taken. Tumor volume was then calculated using the formula provided above. Once the individual tumor volume reached 3,000 mm$^3$ or the tumor ulcerated, the animals would be sacrificed based on IACUC regulations.

The result is shown in the FIG. 1. As is understood from the figure, tumor growth was completely suppressed at varied doses, among which the lowest dose was 40 mg/kg. The results demonstrated that PTX-encapsulated PGGA-hydrotrope III PMs have excellent anticancer efficacy. The dose response was not evident because of complete suppression.

Example 6

Effect of Drug Encapsulated PGGA-Hydrotropepolymer Micelle Compared to Conventional Drug Mice bearing lung cancer xenograft derived from NCI-H460 cell lines (purchased from ATCC) were prepared in the same manner as Example 4. The mice were assigned into the vehicle control and various treatment groups in the same manner to Example 5. As for the assay, the test was performed in a similar manner but slightly modified, such that the Abraxane® (albumin-bound paclitaxel) was administered at a dosage of 80 mg/kg, as a comparison for the same dosage of PTX-PGGA-Hydrotrope III.

Figure 2:
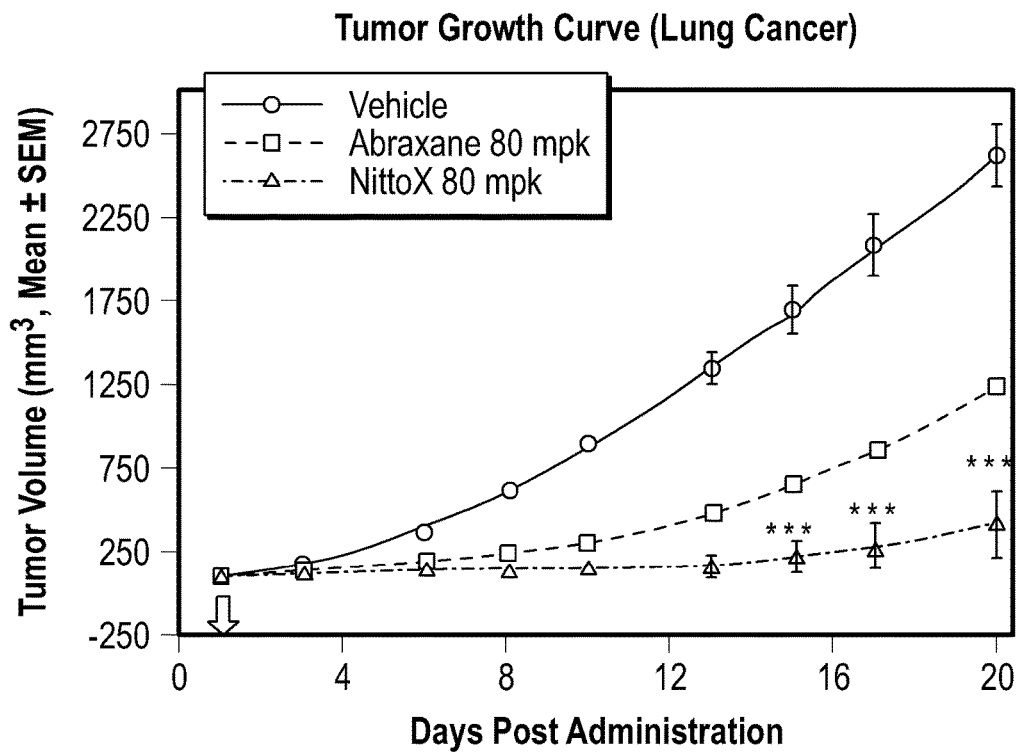
FIG. 2 compares PTX-PGGA-Hydrotrope III with the conventional dosage form of Paclitaxel (Abraxane®) in a lung cancer model, efficacy (upper) and tumor weight on Day 21 post dosing (lower).
Figure 2:
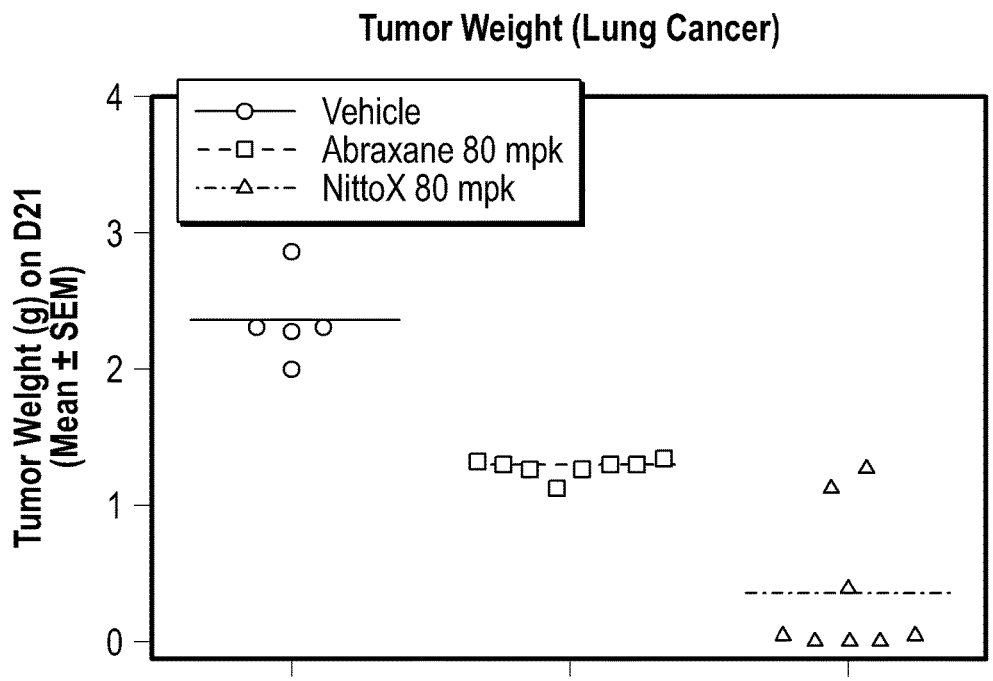

The result is shown in the FIG. 2. As is understood from the figure, the tumor suppression effect of PTX-PGGA-Hydrotrope III is superior to the same dosage of FDA-approved drug Abraxane®.

Example 7

Tumor PK/PD Study

Mice bearing lung cancer xenograft was prepared in the same manner as Example 6. Briefly, cells were harvested at log phase of growth from the tissue culture after lightly trypsinized with trypsin-EDTA. The number of viable cells were counted and determined in a hemocytometer in the presence of trypan blue (only viable cells were counted). Each mouse was inoculated subcutaneously in the right flank with 0.1 mL of an inoculum of 2×10⁶ of NCI-H460 cells using a 25 G needle and syringe, (one inoculum per mouse). Tumor volume was monitored twice a week. Bodyweight measurements were also taken. Tumor volume was calculated using the formula: Tumor volume=(length×(width)²)/2.

Once tumor size reached 500-600 mm³, animals were administered with PTX-PGGA-Hydrotrope III at 100 mg/kg (IV, qd×1). Plasma, tumor and livers were harvested at the indicated time points. Tumor was split into two parts, one for measuring paclitaxel concentration as pharmacokinetics (PK) analysis, and the other for measuring PD (Pharmacodynamics) biomarker including acetylated tubulin and Ki67. One slice of liver was dissected from right lobe of liver for PK analysis. PTX was quantified by LC/MS/MS for PK analysis. For PD analysis, acetylated tubulin was assessed using ELISA method. Briefly, tumor samples were broken down using tissue lysis buffer (Cat: FNN0071, Life Technology) according to manufactory's instruction and the protein in question was quantified subsequently. The expression of acetylated tubulin was examined using ELISA method (Cat: 7204, Cell Signaling). For PD biomarker of Ki67, the sample preparation was the same as described above. The expression of Ki67 was measured using ELISA method (#CSB-E16294).

Figure 3A:
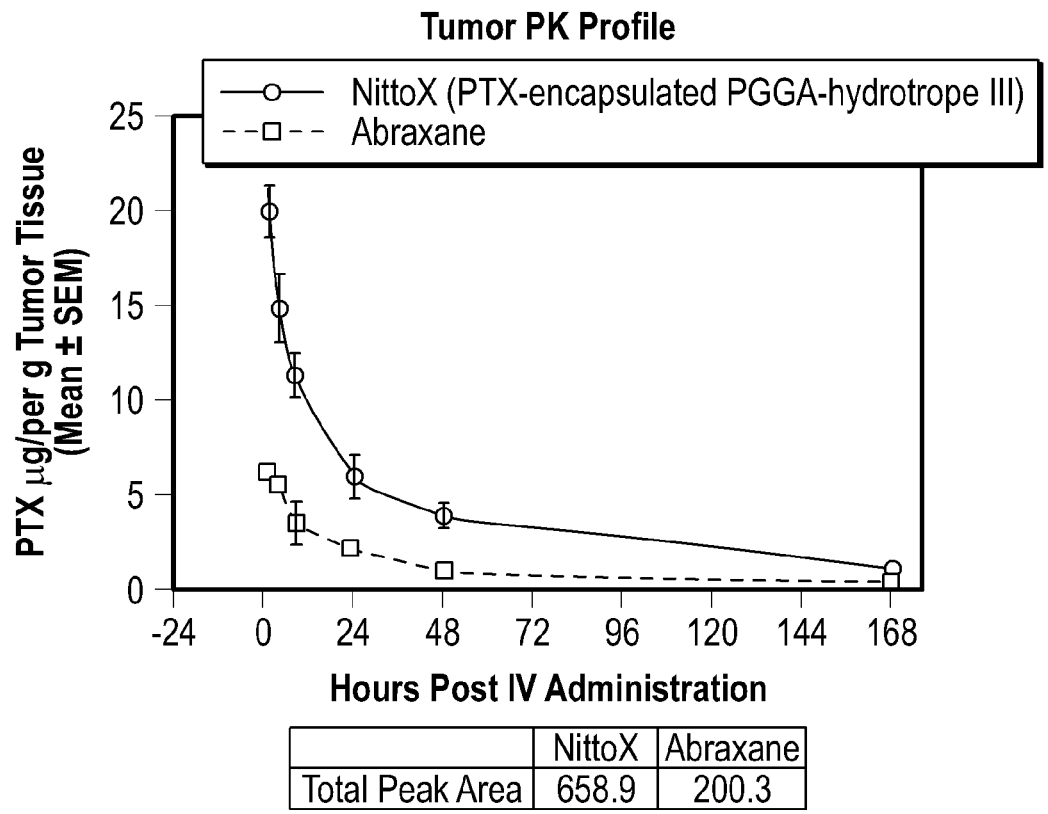
FIGS. 3A and 3B show tumor PK profiles of PTX-PGGA-Hydrotrope III versus Abraxane® in animals bearing NCI-H460 xenograft.
Figure 3A:
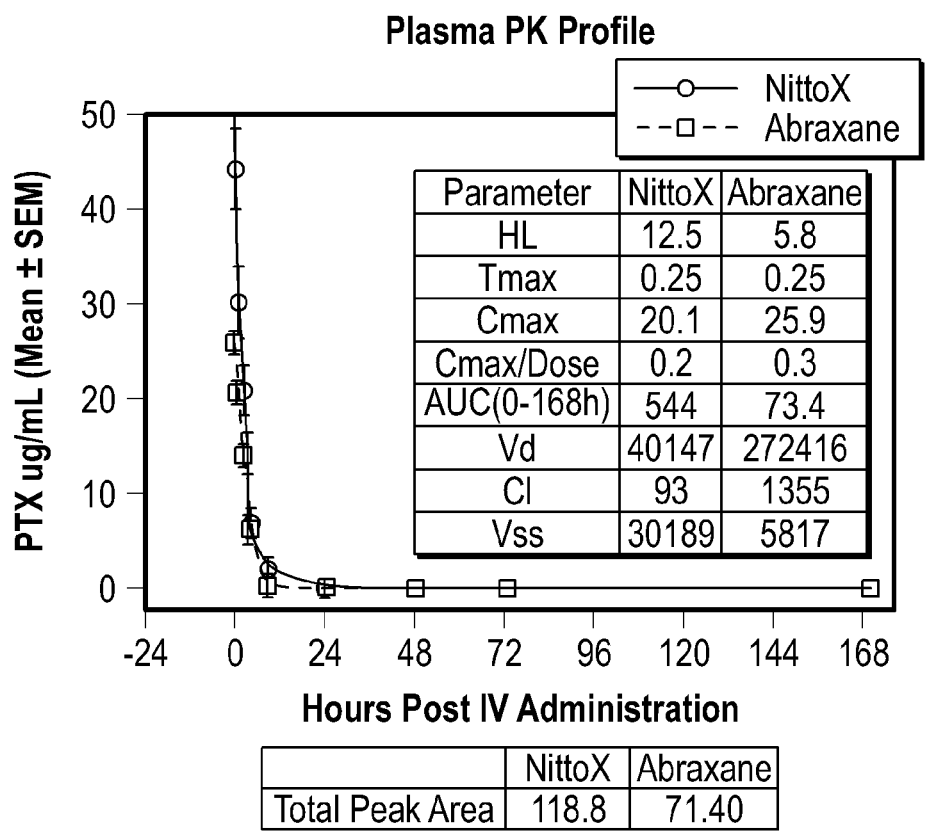
Figure 3B:
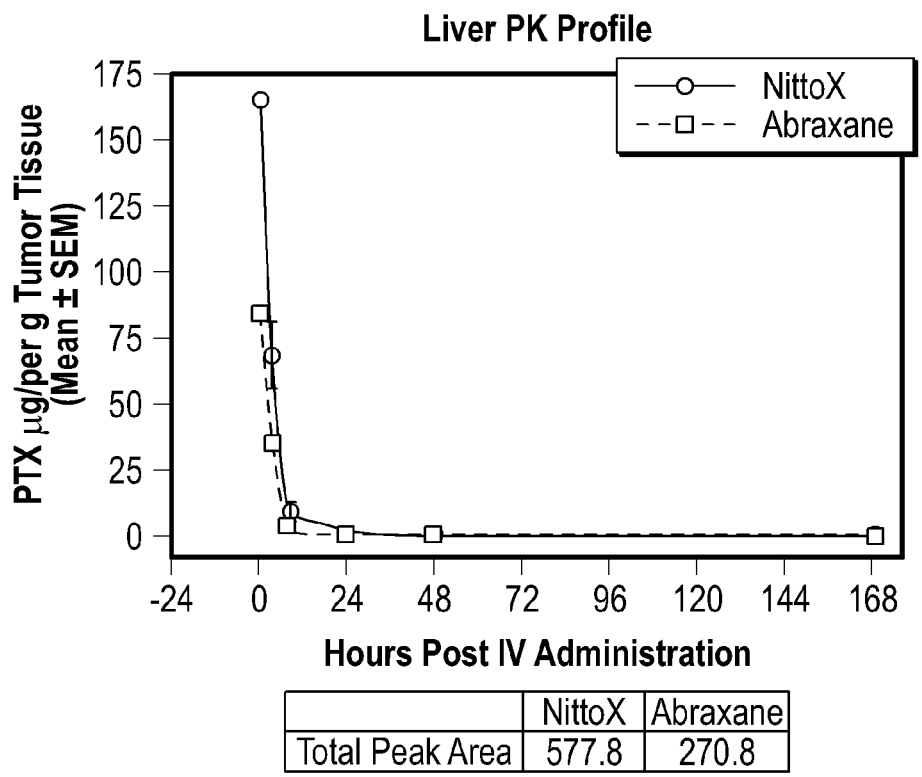
Figure 4A:
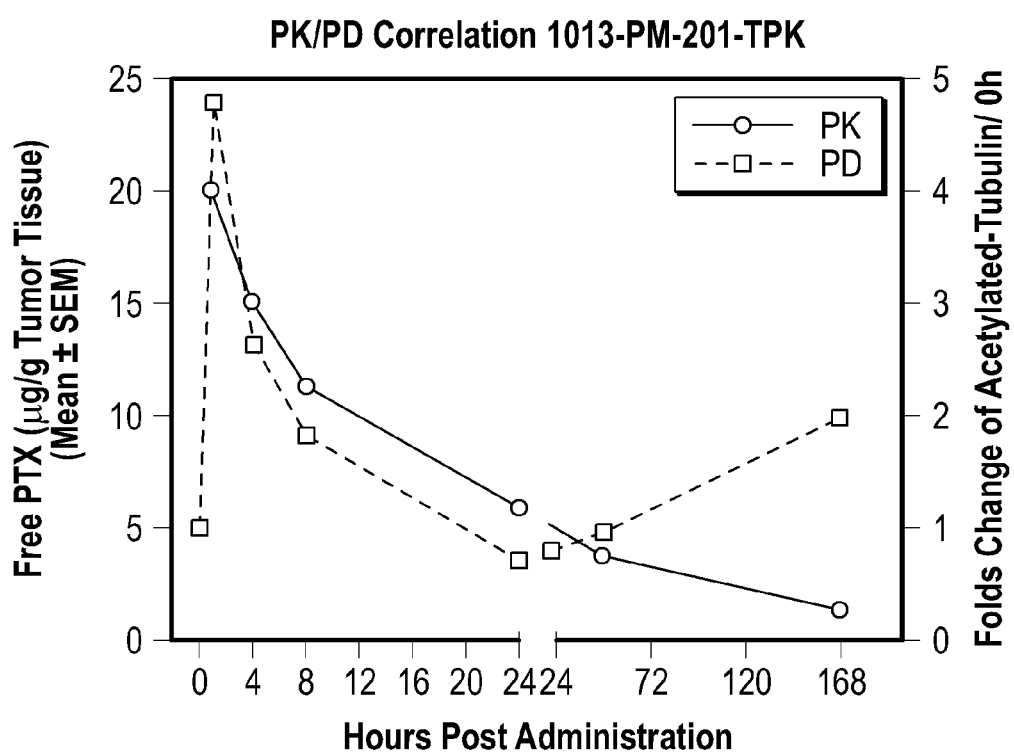
FIG. 4A depicts the PK/PD correlation of PTX-PGGA-Hydrotrope III in animals bearing NCI-H460 xenograft, in which acetylated tubulin was used as a PD biomarker (upper). Expression of Ki67 was also used as a second biomarker to verify the PD data, IHC staining of Ki67 in tumor tissue (FIG. 4B, lower) and the corresponding quantified data plot (FIG. 4B, upper).
Figure 4B:
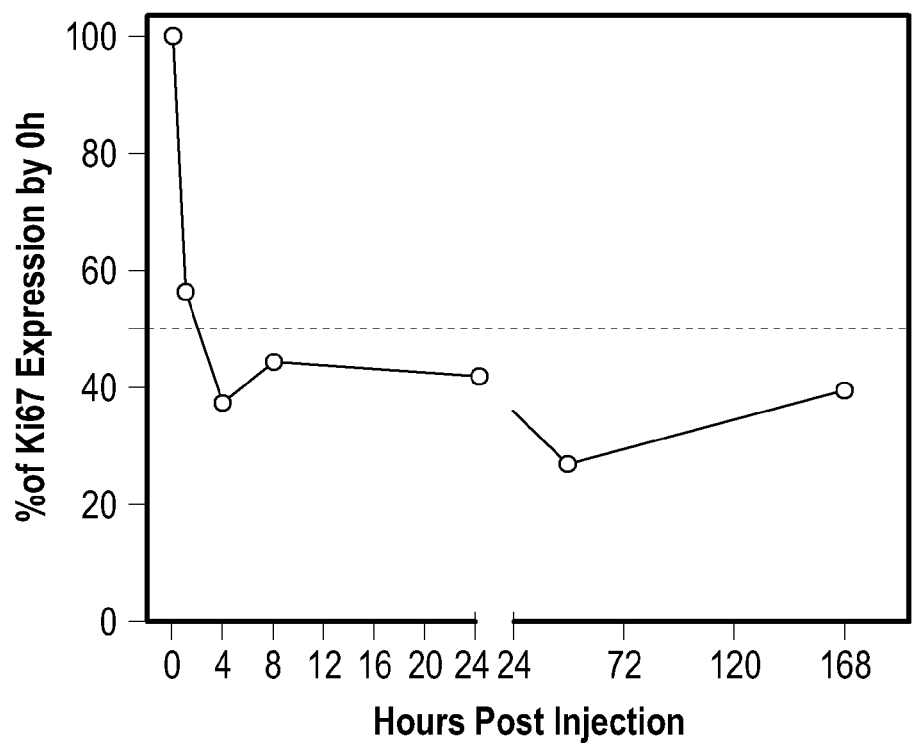
Figure 4B:
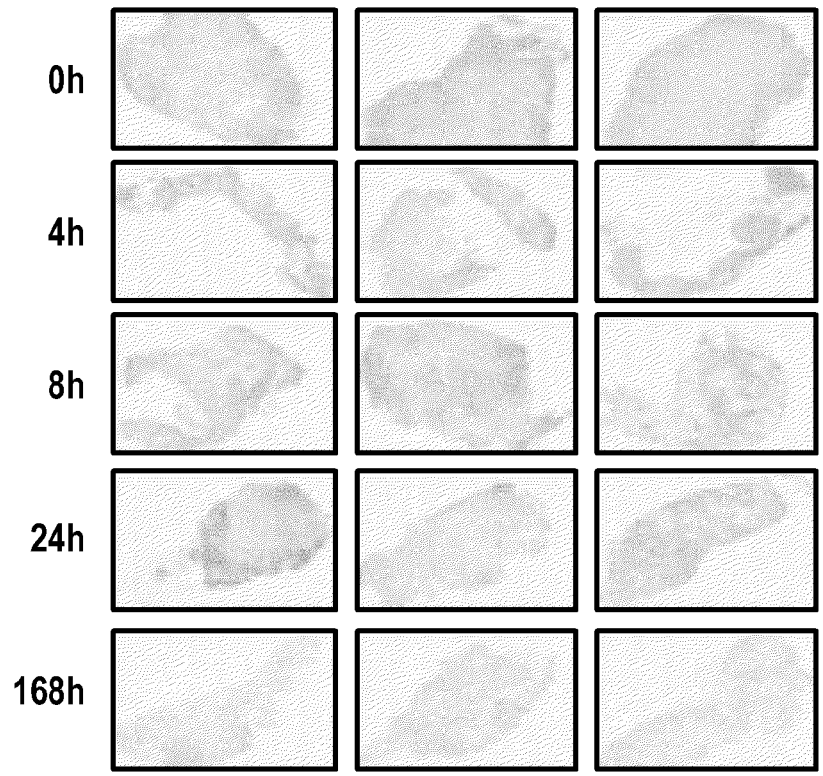

The results are shown in FIGS. 3 and 4. As for tumor PK profile, PTX-PGGA-Hydrotrope III demonstrated three-fold elevation of $C_{max}$ and $AUC_{(0-168\ h)}$ as compared with Abraxane® in tumor, indicating more desirable tumor accumulation was achieved by PTX-PGGA-Hydrotrope III. However, no substantial difference was observed for plasma and liver PK profiles between PTX-PGGA-Hydrotrope III and Abraxane®. As for PD, acetylated tubulin level was increased first but get back within 24 hours. This agreed very well with the corresponding PK data. In addition, expression of Ki67 was also monitored as a second biomarker to verify the PD data. Ki67 level fell down to lower than 40% within 4 hours and stayed around 40% throughout the rest of the experiment. This was again consistent with the PK data.

Example 8

Toxicity Evaluation

Both female and male naïve Balb/C mice at 7-8 week old were purchased from Charles River. Animals were housed and maintained in a controlled environment and all procedures were performed in accordance with Nitto NDT and UCSD IACUC regulations. After acclimation for 5 days, animals were administered with PTX-PGGA-Hydrotrope III at 20, 30 and 40 mpk, (IV, qd ×5). Cage side clinical observation was monitored twice a day and bodyweight was measured daily. At 48 h post dosing, blood samples were harvested and submitted for hematological parameters analysis, including complete blood count (CBC), differentials count, as well as platelet and reticulocyte counts. The data was processed using Prism Graphpad.

Figure 5A:
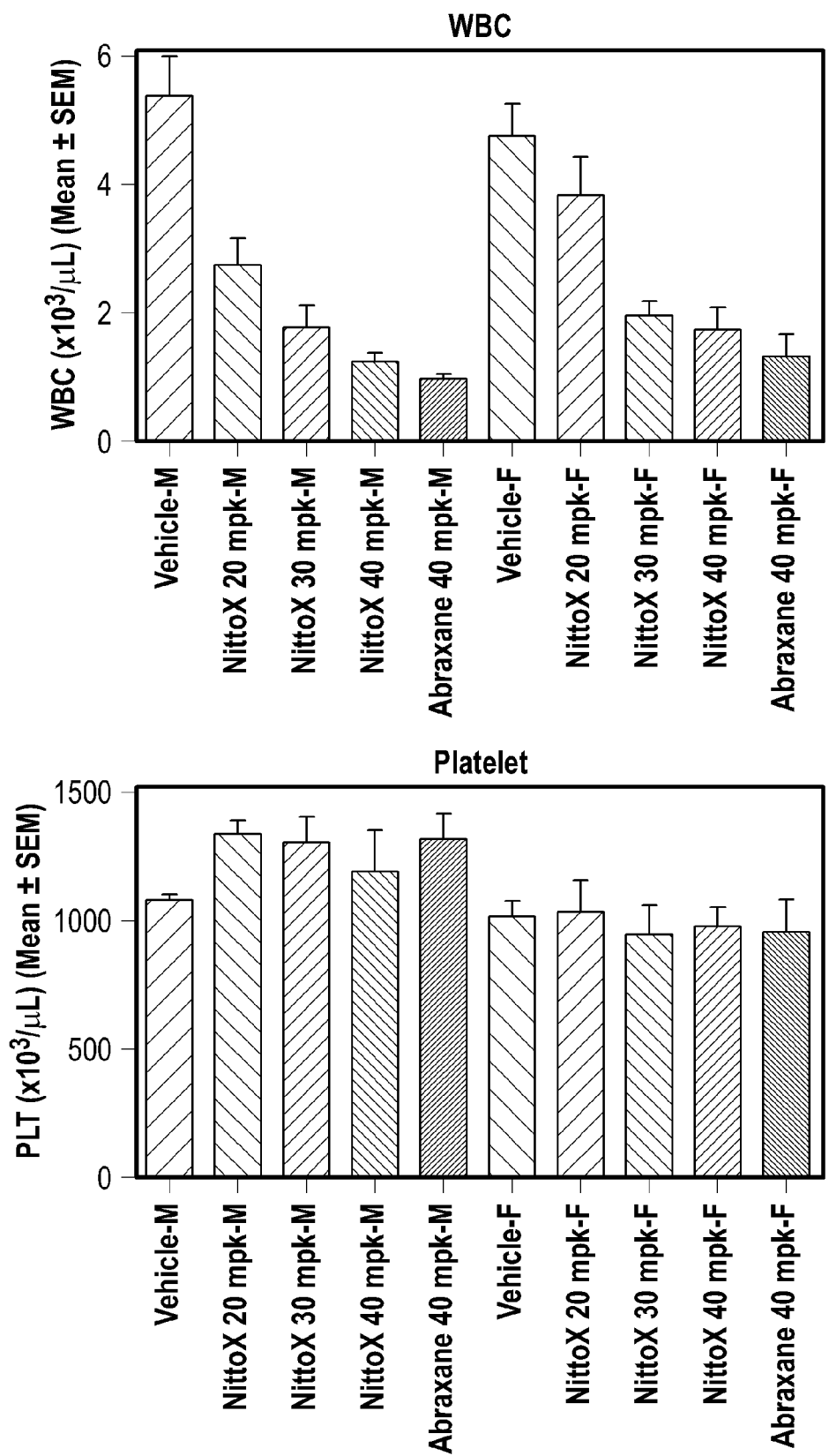
FIGS. 5A-C provide the result of PTX-PGGA-Hydrotrope III toxicity evaluation.
Figure 5B:
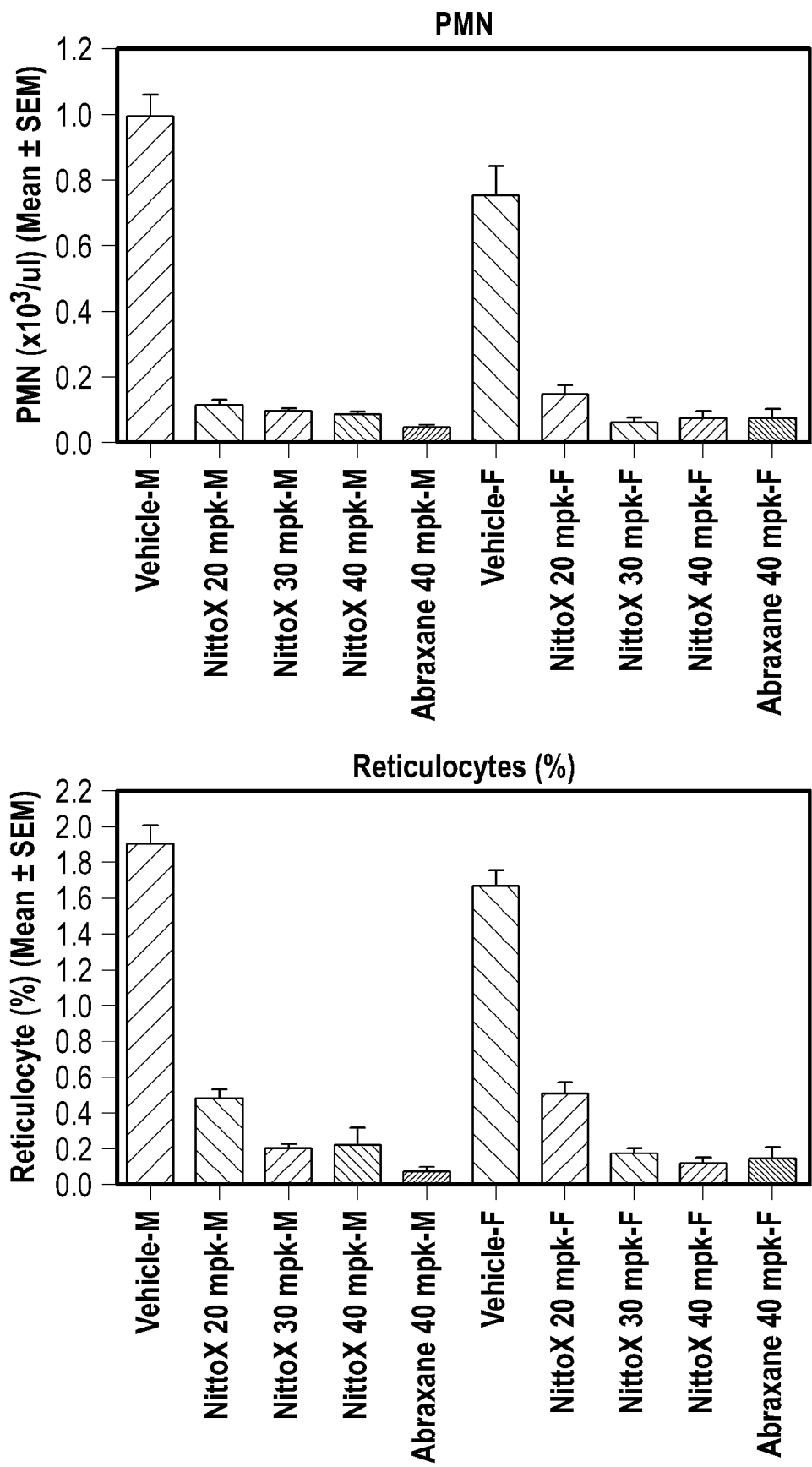
Figure 5C:
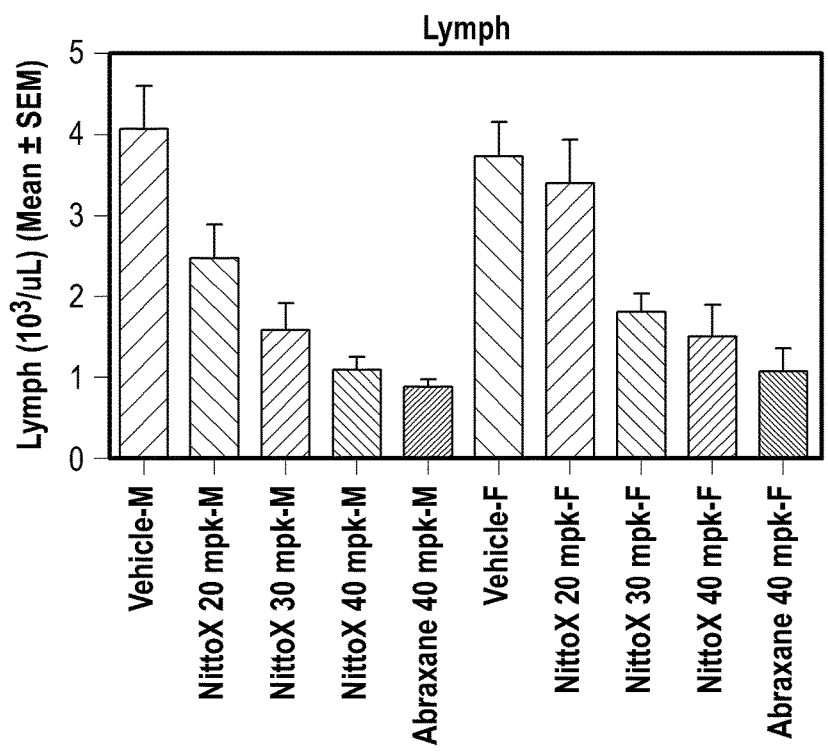
Figure 6:
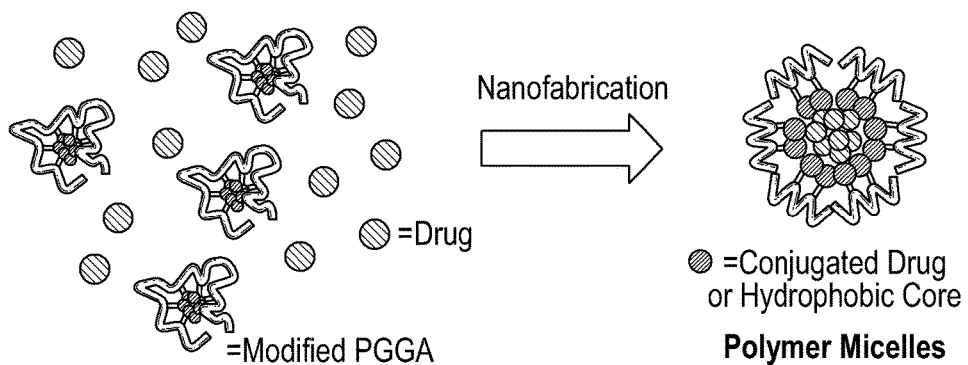
FIG. 6 depicts a schematic diagram of forming an embodiment of the drug encapsulated polymer micelles described herein.

The result is shown in FIG. 5. PTX-PGGA-Hydrotrope III had showed a slightly better tolerability than Abraxane® in terms of toxicity at the same dose level. No gender difference in toxicity was observed.

The results described in these Examples indicate the followings:
  (i) The composition described herein is statistically significantly more efficacious than Abraxane® in NCI-H460 lung cancer xenograft at the same dose level. Dosages are well tolerated by animals in terms of body weight loss and survival. In addition to NCI-H460, The composition described herein is also found remarkably potent in a variety of tumor models, including pancreatic and breast cancers.
  (ii) The improved efficacy is presumably attributed to its superior plasma and tumor pharmacokinetic profile. The composition described herein not only enhances circulation stability over Abraxane®, but also preferentially delivers paclitaxel in three-fold elevation of $C_{max}$ and $AUC_{(0-168\ h)}$ as compared with Abraxane®. Meanwhile, these results are also in accordance with those derived from pharmacodynamic analyses of tubulin polymerization alteration and consequent tumor cell proliferation inhibition. Strong correlation between tumor PK and PD is observed.
  (iii) The composition described herein has also showed a slightly better hematological toxicity than Abraxane®.
  (iv) Taken together, these preclinical data undoubtedly suggest that the composition described herein has potential to be a more potent taxane-based nanomedicine superior to Abraxane®.

It will be understood by those of skill in the art that numerous and various modifications can be made without departing from the spirit of the present invention.

Therefore, it should be clearly understood that the forms of the present invention are illustrative only and not intended to limit the scope of the present invention.

What is claimed is:
1. A polymer conjugate characterized in that the backbone of the polymer is an anionic polymer and hydrophobic moieties are covalently attached to the polymer backbone, comprising monomer units represented by the formula (I) and optionally the formula (II):

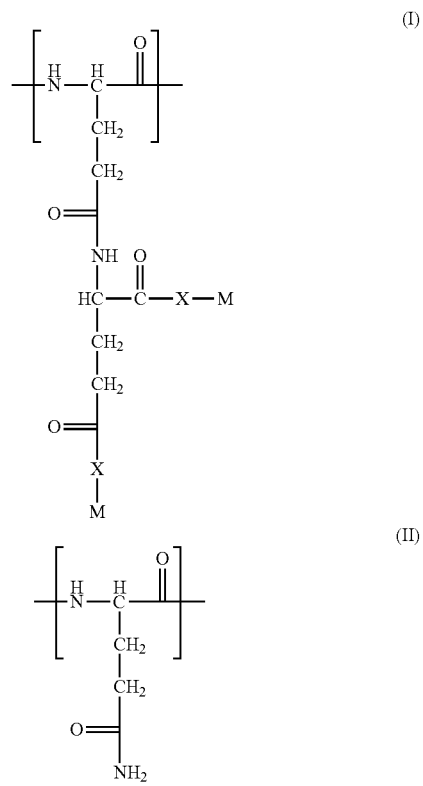

wherein:
M is independently selected from the group consisting of a hydrophobic moiety and a cation; in which the hydrophobic moiety occupies 20-50 mol % of total M amount and the cation occupies the rest of M; and the cation is independently selected from hydrogen, ammonium, or alkali metal;

the hydrophobic moiety is represented by the formula (IV);

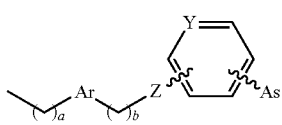

a and b are independently an integer of 0 to 4;
Ar is independently an aryl or heteroaryl;
Z is independently selected from the group consisting of O, S, SO, $SO_2$, NR, and $CR_2$;
Y is CH or N;
As is one to three substituents independently selected from the group consisting of halides, OR, $NR_2$, COOR, $CONR_2$, and CN;
X is independently selected from the group consisting of O, S and NR; and
R is independently selected from the group consisting of H, $C_{1-4}$ alkyl, $C_{2-4}$ alkenyl, $C_{2-4}$ alkynyl, aryl, and heteroaryl.

2. The polymer conjugate according to claim 1, characterized in that the polymer conjugate is represented by the formula (III)

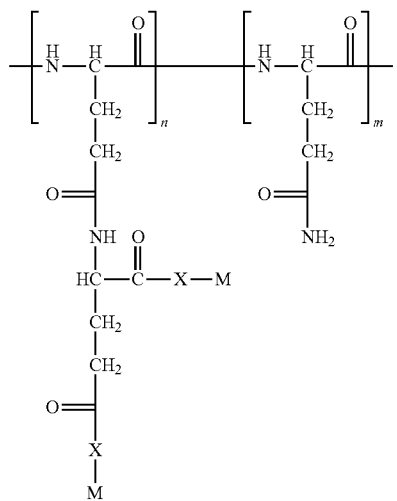

wherein:
m and n are both an integer, where m is 0 or defined such that the ratio of m:n is from 1:9 to 5:5.

3. The polymer conjugate according to claim 1, wherein As is one substituent of $CONR_2$.

4. The polymer conjugate according to claim 3, wherein R is selected from ethyl or methyl.

5. The polymer conjugate according to claim 1, wherein a and b are both 1.

6. The polymer conjugate according to claim 1, wherein Ar is aryl.

7. The polymer conjugate according to claim 1, wherein Z is O.

8. The polymer conjugate according to claim 1, wherein the hydrophobic moiety is independently selected from

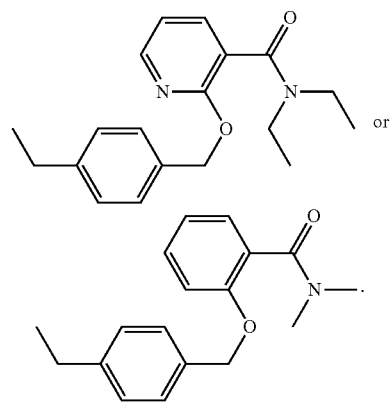

9. A polymer micelle comprising a polymer conjugate according to claim 1.

10. A composition comprising: a carrier comprising the polymer conjugate according to claim 1, and a hydrophobic compound operatively associated with the carrier.

11. A therapeutic composition comprising: a carrier comprising the polymer conjugated according to claim 1, and a hydrophobic drug operatively associated with the carrier.

12. The therapeutic composition according to claim 11, wherein the hydrophobic drug is an anticancer drug.

13. The therapeutic composition according to claim 11, wherein the drug is selected from the group consisting of paclitaxel, docetaxel, tanespimycin, griseofulvin, nifedipine, progesterone, and probucol.

14. The therapeutic composition according to claim 11, wherein the drug is selected from the group consisting of paclitaxel, docetaxel, and tanespimycin.

15. The therapeutic composition according to claim 11, wherein the polymer conjugate forms a polymer micelle and the hydrophobic therapeutic agent is encapsulated in the polymer micelle.

* * * * *